(12) United States Patent
Hart et al.

(10) Patent No.: US 8,152,603 B2
(45) Date of Patent: Apr. 10, 2012

(54) SLIDE HOLDER FOR SAMPLE HOLDER FOR GRINDER/POLISHER

(75) Inventors: Michael F. Hart, Mundelein, IL (US); Lawrence L. Freson, Mount Prospect, IL (US)

(73) Assignee: Illinois Tool Works Inc., Glenview, IL (US)

( * ) Notice: Subject to any disclaimer, the term of this patent is extended or adjusted under 35 U.S.C. 154(b) by 356 days.

(21) Appl. No.: 12/561,926

(22) Filed: Sep. 17, 2009

(65) Prior Publication Data

US 2010/0122591 A1 May 20, 2010

Related U.S. Application Data

(60) Provisional application No. 61/116,405, filed on Nov. 20, 2008.

(51) Int. Cl.
*B24B 19/00* (2006.01)
(52) U.S. Cl. ........................................................ 451/460
(58) Field of Classification Search ........................ None
See application file for complete search history.

(56) References Cited

U.S. PATENT DOCUMENTS

| 4,015,865 A | * | 4/1977 | Kongelka | 285/198 |
| 4,579,313 A | * | 4/1986 | Adani et al. | 249/95 |
| 4,623,500 A | * | 11/1986 | Nelson et al. | 264/162 |

OTHER PUBLICATIONS

International Search Report and Written Opinion issued by the International Searching Authority on Dec. 10, 2009 in connection with PCT/US2009/060937.
Buehler Ltd. 2009 Grinder-Polisher Equipment Guide.

* cited by examiner

*Primary Examiner* — Robert R Raevis
(74) *Attorney, Agent, or Firm* — Levenfeld Pearlstein, LLC

(57) ABSTRACT

A slide holder for mounting to a sample holder having a pair of openings therein, for a grinder/polisher includes a plate for receiving the slide. The slide holder includes a pair of stems extending from the plate and configured and spaced for receipt in the sample holder openings. A locking element is mounted to each stem. The locking elements are mounted to pivot eccentrically relative to a center axis of each stem. The stems are inserted into the sample holder openings and the locking elements are pivoted to lock the slide holder to the sample holder and to prevent the stems from disengaging from the sample holder.

19 Claims, 5 Drawing Sheets

SLIDE HOLDER FOR SAMPLE HOLDER FOR GRINDER/POLISHER

CROSS-REFERENCE TO RELATED APPLICATION DATA

This application claims the benefit of priority of Provisional U.S. Patent Application Ser. No. 61/116,405, filed Nov. 20, 2008.

BACKGROUND OF THE INVENTION

The present invention relates to a grinder/polisher. More particularly, the present invention relates to an improved slide holder for a sample holder for a grinder/polisher.

Grinder/polishers are in use in many industries. They are often used to prepare samples of rocks, metals, polymers, ceramics or the like for further examination, such as by microscopic examination.

Grinder/polishers include a sample or specimen holder that is configured to rotate relative to a platen that is also configured to rotate. In this manner, there are two rotating motions occurring simultaneously. A typical sample holder is a round plate that mounts, at its center, to a chuck. The plate has a multiple openings equally radially spaced and equally circumferentially spaced from one another. For example, the plate can include six (round) openings spaced 60 degrees from one another and equally spaced from the center. The specimens are each mounted to a support and each support is positioned in one of the holder openings. A hold-down finger applies pressure to each support to urge the specimen against the platen. One such grinder/polisher is the EcoMet 250, commercially available from ITW-Buehler of Lake Bluff, Ill. Such a grinder polisher is also disclosed in copending Shewey, U.S. patent application Ser. No. 12/470,757, which is commonly assigned with the present application and which is incorporated herein by reference.

A slurry, generally abrasive, is injected onto the platen to provide an abrasive medium for grinding and polishing the specimen.

Certain samples, such as rocks are typically examined by creating a very thin sample of the rock mounted to a glass slide. The sample is mounted to the slide so that it can be observed through a microscope. In order to grind the sample it is desirable to mount it to the slide prior to grinding so that the thin rock sample is minimally handled after it is prepared. That is, the rock is prepared (ground) mounted to the glass slide.

One known mount or slide holder for the glass slide includes a plate that mounts to the bottom of the sample holder. The plate has pair of spaced apart stems that insert up, into the openings in the holder. During the grinding/polishing process the hold-down fingers apply a pressure on the stems which in turn urges the sample into contact with the platen. The stems each include an o-ring positioned about the stem to create a friction fit between the stem and the opening in the sample holder.

While such an arrangement functions well, it has been observed that the slide holder can become difficult to remove from the holder (the stem becomes stuck in the opening), or conversely, the stem is not adequately friction fit (e.g., not secured) in the opening and can fall out when the sample holder is raised from the platen.

Accordingly, there is a need for an improved slide holder for use in a grinder/polisher sample holder. Desirably, such a slide holder positively holds a slide thereto for preparation for examination. More desirably, such a slide holder is easily positioned in the sample holder and is secured or locked in place during the grinding/polishing process and is readily released from the sample holder for examination, further processing or the like.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying and drawings, wherein.

DETAILED DESCRIPTION OF THE INVENTION

Figure 1:
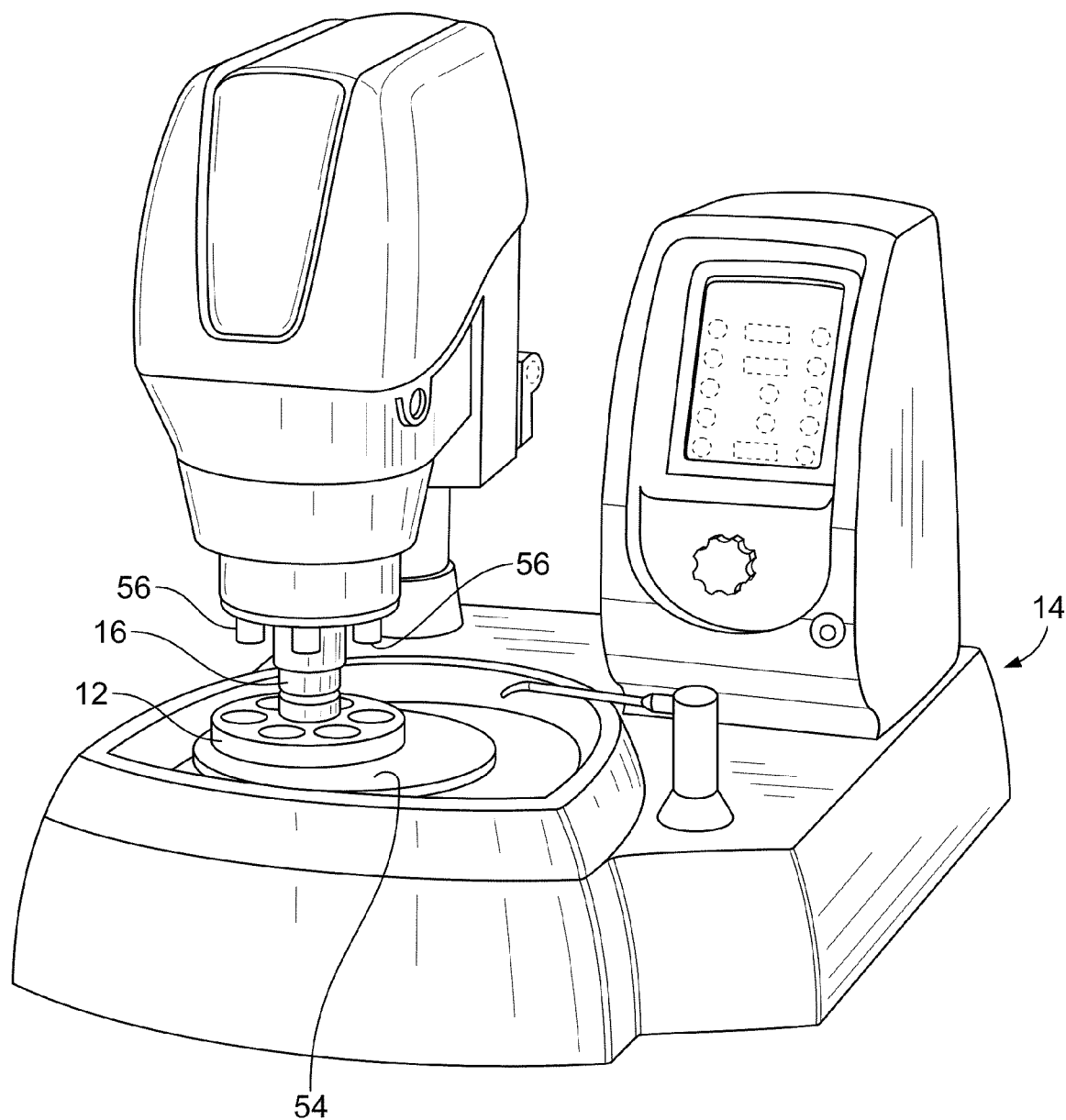
FIG. 1 is a perspective view of a grinder/polisher in which a slide holder for a sample holder embodying the principles of the present invention is used.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Figure 2:
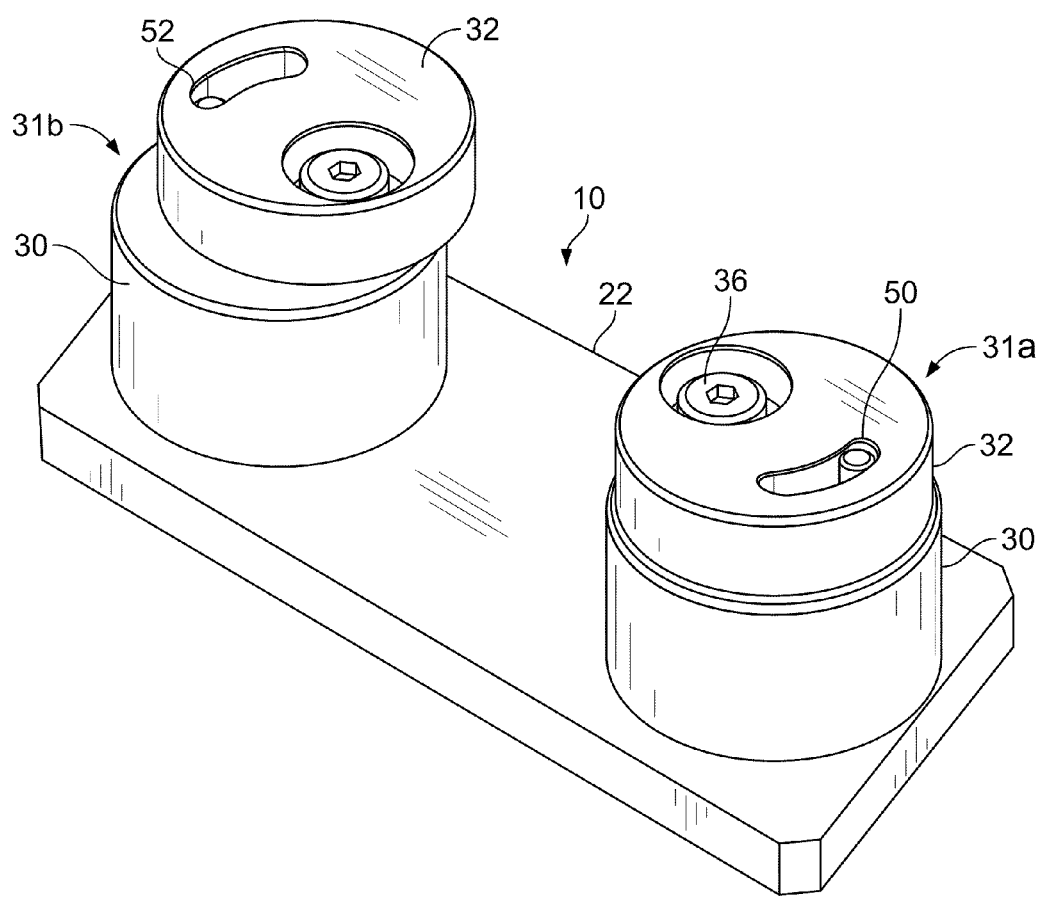
FIG. 2 is a perspective view of the slide holder embodying the principles of the present invention.
Figure 3:
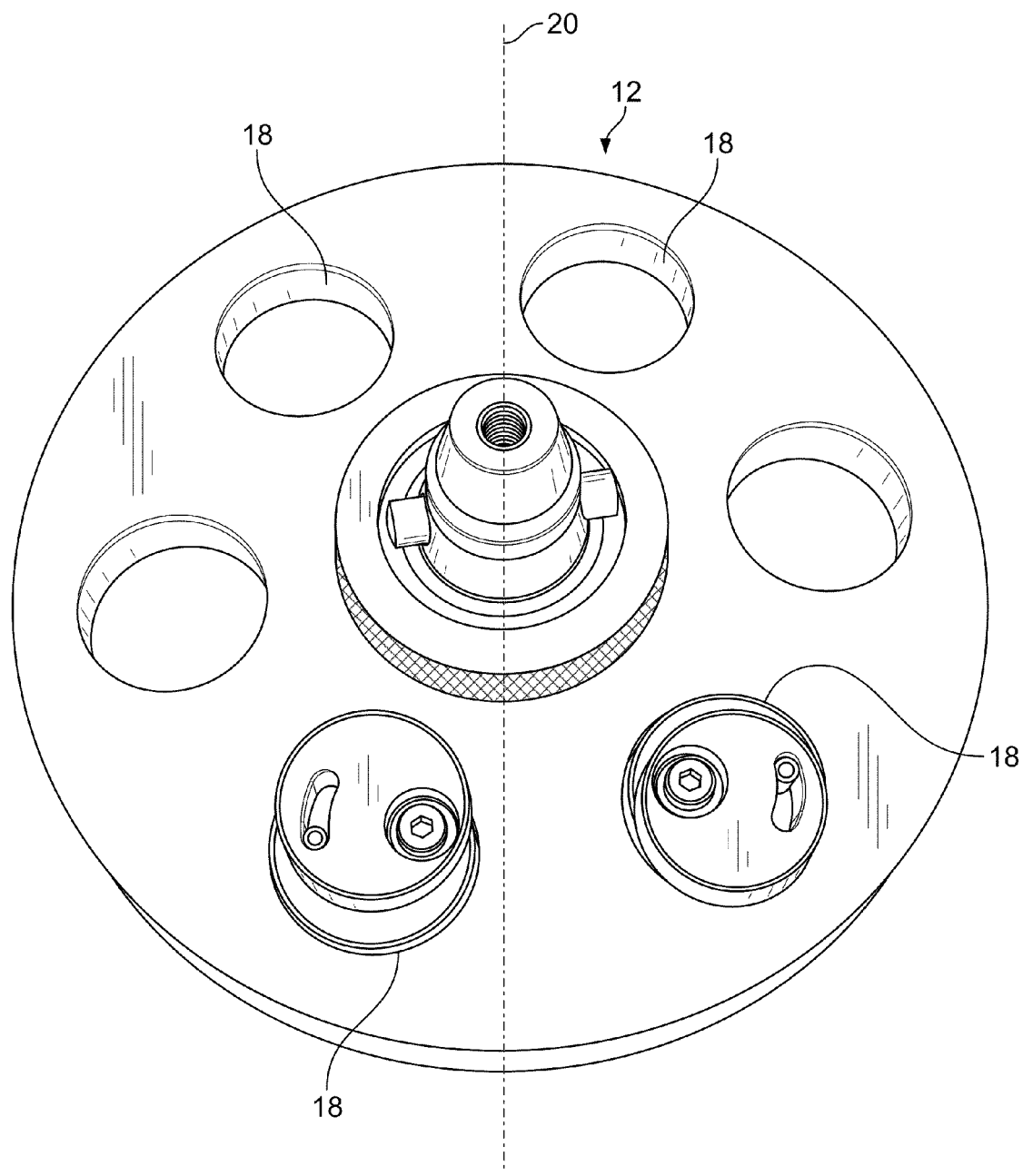
FIG. 3 is a top view of the slide holder positioned in a sample holder.

Referring now to the figures and in particular, to FIGS. 1 and 2, there are shown a slide holder 10 (FIG. 2) for a sample holder 12 for a grinder/polisher 14 (FIG. 1) embodying the principles of the present invention. In FIG. 3, the slide holder 10 is shown mounted to the sample holder 12. The sample holder 12 is in turn mounted to the chuck 16 of the grinder/polisher 14 (FIG. 1). The illustrated sample holder 12 has six openings 18 that are equally radially spaced from the center 20 of the sample holder 12 and that are equally circumferentially spaced from one another (60 degrees apart from adjacent openings).

The slide holder 10 includes a plate 22. On one side 24 of the plate 22 a glass slide or the like 26 can be mounted on which the sample or specimen S is mounted. In a typical petrographic arrangement, for example, a rock is secured to the glass side 26 (opposite of the side of the glass 26 mounted to the plate 22), by an adhesive D, cement, wax or the like.

On the opposite side 28 of the plate 22, the slide holder 10 includes a pair of stems 30 fixedly mounted to the plate 22. The stems 30 are spaced from one another and configured to insert into two of the openings 18 in the sample holder 12. In a present slide holder 10, the stems 30 have a height $h_{30}$ that is greater than the thickness $t_{12}$ of the sample holder 12.

The stems 30 each have an eccentrically mounted locking element 32 mounted to the top 34 of the stem 30. The locking element 32 pivots about a pivot pin 36 or shoulder bolt that permits the locking element 32 to move relative to the stem 30. In a present embodiment, the locking element is eccentrically mounted (as at 38) to the stem 30 so that locking element axis $A_{32}$ and stem axis $A_{30}$ are moved into and out of alignment with one another. Referring to FIG. 2, when the element 32 and stem 30 are aligned (as indicated at 31a), the periphery or footprint of the locking element 32 is coincident with or subsumed within the periphery or bounds of the stem 30. When they are not aligned (as indicated at 31b), a portion of the element 32 extends over the periphery of the stem 30.

The pin 36 can insert into a well 40 in the top 42 of the locking element 32 so that, as seen in a preferred embodiment, the pin 36 does not extend above the top 42 of the element 32. A wave washer 44 or like member 44 is positioned between the pin 36 (bolt) and the element 32 to provide frictional resistance to pivoting of the element 32. In this manner, the washer 44 locks the element 32 in a secure state on the stem 30.

To prevent the element 32 from over pivoting or over rotating on the stem 30, a stop pin 46 is mounted to and extends upward from the stem 30. The stop pin 46 is positioned in an arcuate notch or opening 48 in the locking element 32. In this manner, the stop pin 46 provides the bounds between which the locking element 32 can pivot or rotate. One bound or end of the notch (as indicated at 50 in FIG. 2) is disposed to concentrically align the locking element 32 and the stem 30, and the other bound or end of the notch (as indicated 52 at in FIG. 2) is disposed such that the locking element 32 is eccentric of the stem 30. In a present slide holder 10, the locking element 32 has a diameter $d_{32}$ that is slightly less than the diameter $d_{30}$ of the stem 30 to permit the stem 30 (and locking element 32) to be readily inserted into the sample holder opening 18.

Figure 4:
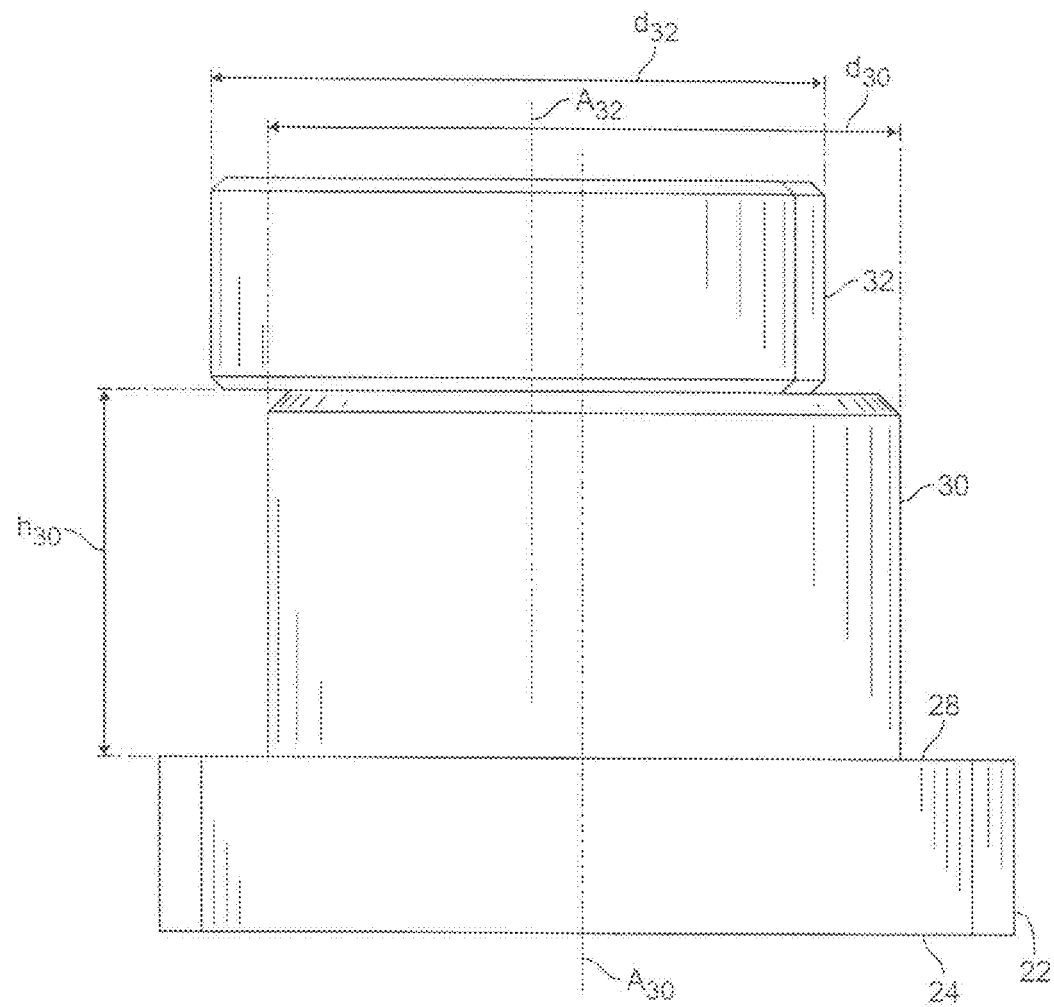
FIG. 4 is a side view of the slide holder of FIG. 2.
Figure 5:
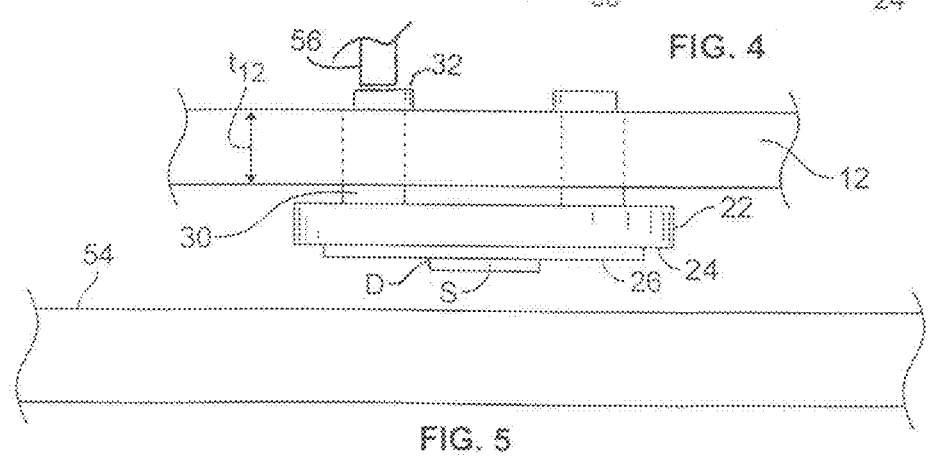
FIG. 5 is a schematic illustration of the slide holder with a slide and sample mounted in a sample holder and positioned in proximity to the grinder/polisher platen.
Figure 6:
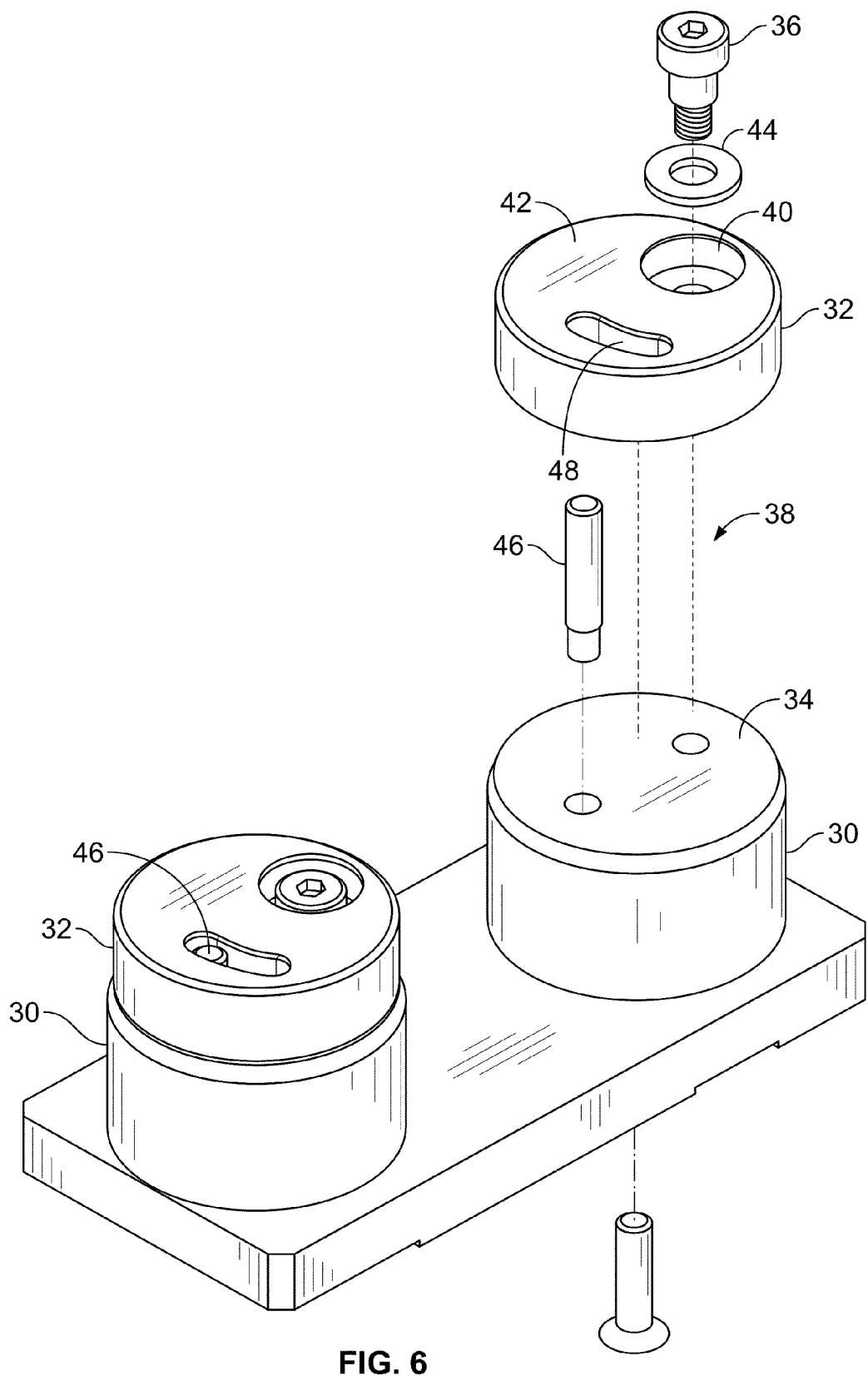
FIG. 6 is a partially exploded view of the slide holder.

In use, a sample S is mounted to the glass slide 26 and the glass slide 26 is mounted to the slide holder 10. The locking elements 32 are pivoted to align with the stems 30 and the stems 30 (and elements 32) are inserted into the openings 18 of the sample holder 12. Once the stems 30 (and elements 32) extend through the openings 18, the locking elements 32 are rotated to the locked position (see FIG. 3). The sample holder 12 (which is installed in the grinder/polisher chuck 16) is then lowered to bring the sample S into contact with the platen 54, and the hold-down fingers 56 are lowered into contact with the locking elements 32. The grinder/polisher 14 is then started to grind the sample S as desired. It will be appreciated that the hold down fingers 56 are aligned with the stems 30 and elements 32 (see FIG. 4). As such, pressure from the fingers 56 is transmitted through the elements 32 and stems 30, through the slide holder 10 and into the sample S.

After the grinding/polishing operation is complete, the fingers 56 are moved away from the locking elements 32, the sample holder 12 is raised away from the platen 54, and the locking elements 32 are rotated into alignment with the stems 30 to remove the slide holder 10 and sample S.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the invention.

What is claimed is:

1. A slide holder for mounting a slide to a sample holder for use in a grinder/polisher, the sample holder having a pair of openings therein spaced from one another a predetermined distance and having a thickness, the slide holder comprising:
   a plate for carrying the slide;
   a pair of stems extending from the plate, the stems spaced from one another a distance equal to the predetermined distance between the sample holder openings, the stems configured for receipt in the sample holder openings, the stems having an axis and an outer periphery and having a height;
   a locking element mounted to each stem, the locking elements having an outer periphery, the locking elements mounted on their respective stems to move relative to the axis of its respective stem between a first position in which the periphery of the locking element is coincident with or within the periphery of the stem and a second position in which the periphery of the locking element is, in part, outside of the periphery of the stem,
   wherein the stems are inserted into the sample holder openings with the locking elements in the first position and wherein the locking elements are moved to the second position to lock the slide holder to the sample holder and to prevent the stems from disengaging from the sample holder.

2. The slide holder in accordance with claim 1 wherein the locking elements are pivotable on the stems.

3. The slide holder in accordance with claim 2 wherein the locking elements are eccentrically mounted to the stems.

4. The slide holder in accordance with claim 1 wherein the stems have a circular cross-section having a diameter and the locking elements have a circular cross-section having a diameter.

5. The slide holder in accordance with claim 4 wherein the diameter of each stem is equal to or greater than that the diameter of it respective locking element.

6. The slide holder in accordance with claim 5 wherein the diameter of each stem is greater than the diameter of its respective locking element.

7. The slide holder in accordance with claim 1 including a securing member to secure the locking element is a desired position.

8. The slide holder in accordance with claim 7 wherein the securing member is a wave washer to secure the locking element relative to the stem.

9. The slide holder in accordance with claim 8 where in the locking element is mounted to the stem by a pivot pin and wherein the wave washer is mounted for cooperation with the pivot pin.

10. The slide holder in accordance with claim 1 wherein the stems and the locking elements include cooperating stop pins and openings to limit movement of the locking element relative to the stem.

11. The slide holder in accordance with claim 10 wherein each cooperating stop pin is located on the stem and the opening is located on the locking element.

12. The slide holder in accordance with claim 11 wherein each locking element is pivotable on the stem and wherein the opening is arcuate.

13. The slide holder in accordance with claim 1 wherein the height of the stem is greater than the thickness of the sample holder.

14. A slide holder for mounting a slide to a sample holder for use in a grinder/polisher, the sample holder having a pair of openings therein spaced from one another a predetermined distance and having a thickness, the slide holder comprising:

a plate for carrying the slide;

a pair of cylindrical stems extending from the plate, the stems spaced from one another a distance equal to the predetermined distance between the sample holder openings, the stems configured for receipt in the sample holder openings, the stems having an axis and a diameter and having a height;

a cylindrical locking element mounted to each stem, the locking elements having a diameter less than or equal to the diameter of its respective stem, the locking elements mounted on their respective stems to move relative to the axis of its respective stem between a first position in which the locking element and its respective stem are is coaxial and a second position in which the locking element and its respective stem are eccentric, wherein the stems are inserted into the sample holder openings with the locking elements in the first position and wherein the locking elements are moved to the second position to lock the slide holder to the sample holder and to prevent the stems from disengaging from the sample holder.

15. The slide holder in accordance with claim 14 wherein the locking elements are pivotable on the stems.

16. The slide holder in accordance with claim 14 including a securing member to secure the locking element is a desired position.

17. The slide holder in accordance with claim 14 wherein the stems and the locking elements include cooperating stop pins and openings to limit movement of the locking element relative to the stem.

18. The slide holder in accordance with claim 17 wherein each cooperating stop pin is located on the stem and the opening is located on the locking element.

19. The slide holder in accordance with claim 18 wherein each locking element is pivotable on the stem and wherein the opening is arcuate.

* * * * *

UNITED STATES PATENT AND TRADEMARK OFFICE
CERTIFICATE OF CORRECTION

| | |
|---|---|
| PATENT NO. | : 8,152,603 B2 |
| APPLICATION NO. | : 12/561926 |
| DATED | : April 10, 2012 |
| INVENTOR(S) | : Michael F. Hart and Lawrence L. Freson |

It is certified that error appears in the above-identified patent and that said Letters Patent is hereby corrected as shown below:

In claim 5, Col. 4, line 37, the phrase "diameter of it respective locking element" should read "diameter of its respective locking element".

In claim 7, Col. 4, line 43, the phrase "is a desired position" should read "in a desired position".

In claim 14, Col. 5, lines 14-15, the phrase "are is coaxial" should read "are coaxial".

In claim 16, Col. 6, lines 7-8, the phrase "element is a desired position" should read "element in a desired position".

Signed and Sealed this
Twenty-ninth Day of May, 2012

David J. Kappos
*Director of the United States Patent and Trademark Office*